United States Patent [19]
McDermott et al.

[11] 3,932,277

[45] Jan. 13, 1976

[54] METHOD AND APPARATUS FOR SEPARATING BLOOD FRACTIONS

[75] Inventors: Clifton Eugene McDermott; Franklin Dee Wareham, both of Salt Lake City, Utah

[73] Assignee: Bio-Logics Products, Inc., Salt Lake City, Utah

[22] Filed: Mar. 29, 1974

[21] Appl. No.: 456,168

[52] U.S. Cl................... 210/77; 23/230 B; 23/259; 210/83; 210/359; 210/DIG. 23
[51] Int. Cl.².................. B01D 33/00; G01N 33/16
[58] Field of Search.................. 23/259, 292, 230 B; 210/DIG. 23, 83, 359, 77, 78; 128/2 F, 2 G, 272, DIG. 5; 233/26

[56] References Cited
UNITED STATES PATENTS

| | | | |
|---|---|---|---|
| 3,481,477 | 12/1969 | Farr | 23/259 X |
| 3,508,653 | 4/1970 | Coleman | 233/26 X |
| 3,586,064 | 6/1971 | Brown et al. | 23/259 X |
| 3,661,265 | 5/1972 | Greenspan | 210/359 |
| 3,693,804 | 9/1972 | Grover | 210/359 |
| 3,799,342 | 3/1974 | Greenspan | 210/359 X |
| 3,814,258 | 6/1974 | Ayres | 210/359 |
| 3,832,141 | 8/1974 | Haldopoulos | 23/259 |
| 3,846,077 | 11/1974 | Ohringer | 210/359 X |

*Primary Examiner*—Morris O. Wolk
*Assistant Examiner*—Timothy W. Hagan
*Attorney, Agent, or Firm*—Criddle & Thorpe

[57] ABSTRACT

Method and apparatus for filtering and permanently separating the serum fraction from the cell fraction of centrifuged blood and the like. A separator head is passed through the serum and is positioned at the interface of the serum and the heavier red cells. As the separator head is positioned serum passes through a self-sealing passage in the separator head and into a collection tube that positions the separator head. Upon withdrawal of the collection tube the passage in the separator head closes sufficiently to effectively block the passage and the serum can be poured from the collection tube. The collection tube can be reinserted to pour off measured volumes of the serum.

18 Claims, 4 Drawing Figures

METHOD AND APPARATUS FOR SEPARATING BLOOD FRACTIONS

BRIEF DESCRIPTION OF THE INVENTION

This invention relates to apparatus for the handling of blood samples and the like.

PRIOR ART

The necessity and desirability of separating blood samples into red cells and serum and of being able to separately use the separated fractions for test purposes have long been recognized. It has also been well known that such separation can be obtained by spinning. During such an operation, the red cells gravitate to the bottom of the container in which the sample is placed and the serum moves to the top of the container. While a definite interface is provided between the cells and the serum, the serum constituent is not entirely clear and may contain stringy fibers. As a result, it is frequently desirable that some means be provided to filter the serum to remove such fibers, either during separation of the cells from the serum or afterwards.

In the past, various devices have been provided to separate the serum from the cells. Those with which we are familiar include a collection tube with a sealing head on one end that is inserted into a sample containing tube. The sealing head tightly engages and seals against the inner wall of the sample containing tube and as the sealing head is pushed through the serum to the interface the serum moves through a small orifice in the head and through a small diameter tubing extending beyond the uppermost end of the collection tube and curving downwardly thereinto. The serum passing through the tubing is trapped in the collection tube. When the sealing head is pulled from the sample containing tube, the serum in the tubing will drain back into the sample containing tube. While the collection tube is in place within the sample containing tube the serum collected within the collection tube can be poured off, but some cell material or other non-serum fraction may also pass through the tubing during the pour and since no filter is provided it is possible that some fibrous material can pass through the tubing and into the collection tube.

Other known devices provide a collection tube with a sealing head on one end to make a good sealed contact between the collection tube and the interior wall of a sample. The sealing head has a porous filter and, as the collection tube is moved into the sample containing tube to the interface level the serum is forced through the filter and into the collection tube. Filtered serum can then be poured from the collection tube, or the top of the tube can be stoppered and the collection tube, with the filtered serum therein, can be removed from the sample containing tube. Differential pressure holds the serum in the collection tube during such withdrawal and some loss of the serum occurs back through the filter as the collection tube is pulled out of the sample containing tube.

To our knowledge, there has not heretofore been available apparatus for essentially permanently separating the serum from the cells, while filtering the serum. Neither has there been available apparatus that will allow desired measured amounts of the serum to be selectively drawn off the tube without affecting the remaining serum in the tube or the cell fraction of the sample.

SUMMARY OF THE INVENTION

Principal objects of the present invention are to provide apparatus that will filter and separate serum from cells of a blood sample and that will essentially permanently stopper the cell fraction in the sample container.

Other objects are to provide apparatus by which the entire serum fraction, or any desired portions thereof, can be removed from the sample.

Still another object is to provide apparatus for the handling of blood samples in a safe and effective manner, without exposing persons handling the apparatus to possible contamination from the sample.

Principal features of the invention include a collection tube with a separable sealing head on one end thereof. A self-sealing orifice is provided through the sealing head and all liquid passing through the orifice is filtered through a porous filter. A small diameter orifice tube projects from the bottom of the collection tube to be inserted into the self-sealing orifice and the orifice tube opens into the collection tube. If desired, a sample cup having a base constructed in conventional fashion to fit onto testing equipment can be provided with a rim adapted to telescope onto the otherwise open end of the collection tube.

Further objects and features of the invention will become apparent from the following detailed description and drawing, disclosing what is presently contemplated as being the best mode of the invention.

THE DRAWINGS

In the drawings:

FIG. 1 is a side elevation view of the collection tube and attached separable sealing head of the invention;

FIG. 2, an enlarged vertical section, taken on the line 2—2 of FIG. 1;

FIG. 3, a side elevation view of the collection tube and sealing head of FIG. 1, shown with the sealing head positioned at the interface of a spun blood sample in a sample container; and FIG. 4, a view like that of FIG. 3, but with the sealing head essentially permanently positioned at the interface, the collection tube partially removed, and a sample cup telescoped over the otherwise fully open end of the collection tube.

DETAILED DESCRIPTION

Figures 1, 2, 3, 4:
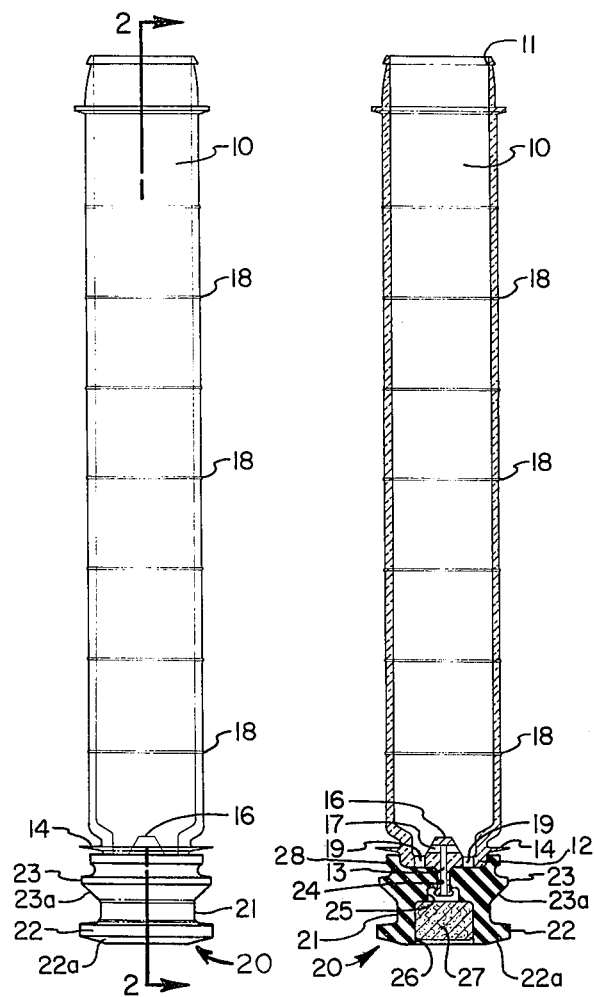

Referring now to the drawings:

In the illustrated preferred embodiment, a collection tube, shown generally at 10, is of generally cylindrical configuration and has a fully open end 11 and a substantially closed end 12 from which a small diameter orifice tube 13 projects. A flexible ring 14 projects outwardly from the collection tube at the end 12, such that the ring will serve as a seal, in a manner to be hereinafter explained.

Orifice tube 13 extends into the interior of collection tube 10 and opens into a spray guard 16 that is positioned within the collection tube 10 and that has at least one passage 17 extending transversely to the bore of the orifice tube and through which liquid entering the orifice tube must pass before entering the collection tube. As will be further explained, the spray guard keeps liquid being forced through the orifice tube from being ejected out of the open end of the collection tube.

A series of markings 18 are provided on the wall of collection tube 10 to indicate the volume of liquid present in the tube and a plurality of drain holes 19 extend through the closed end.

A sealing head, shown generally at 20, is provided to be mounted at the substantially closed end 12 of collection tube 10.

The sealing head 20 includes a body 21 made of resilient material such as rubber or thermoplastic elustomer, and having a pair of spaced apart, outwardly projecting sealing flanges 22 and 23. Each of the flanges 22 and 23 has an inclined face (22a and 23a, respectively) for purposes to be explained. A very small diameter bore hole 24 extends from one face of body 21 to an intermediate cavity 25 that is connected to a large counterbore 26, extending to an opposite face of the body 21. A porous filter 27, made of a porous cellular material such as a suitable reticulated plastic foam or a ceramic, for example, fits tightly in the counterbore 26.

In assembling the sealing head 20 onto the collection tube 10, the orifice tube 13 is inserted into the bore 24 which, in the relaxed state of head 20, has a diameter that is considerably smaller than the outer diameter of the orifice tube 13 and which, because of the configuration of the head, is normally closed to flow therethrough. As the larger orifice tube 13 is inserted through the bore 24 the portion of the head 21 surrounding the bore compresses and is deformed into the cavity 25. When the orifice tube is fully inserted into bore 24, the end 12 of the collection tube is abutting the body 21 and fits within a ring portion 28 of the body and the orifice tube 13 opens into cavity 25, a spaced distance from the filter 27. With the collection tube and orifice tube so assembled, liquid can move into counterbore 26, through filter 27, into cavity 25, and then into the collection tube through orifice tube 13 and passages 17. The volume of liquid within the collection tube at any given time is determined by reading of the markings 18 in conventional fashion.

The assembled collection tube 10 and head 20 comprise a separator unit, adapted to be used with a standard test tube-type collection vessel 29, in which blood samples are collected and centrifuged.

After the blood sample in vessel 29 has been centrifuged, the red cells 30 of the sample are collected as a cell fraction at the bottom of the tube and the lighter serum portion of the sample forms a serum fraction 31 (FIGS. 3 and 4) above the collected red cells. A rather well defined interface can be observed between the sample fractions.

The separator unit comprising the collection tube and head is used to permanently separate the sample fractions and to allow removal of all or any selected portions of the serum fraction.

In use, the separator unit is inserted, with the end having head 20 thereon leading downwardly, into the vessel 29. As the head 20 moves into the open end of vessel 29 the inclined faces 22a and 23a of the resilient flanges 22 and 23 engage the open end of vessel 29 and guide the head into the vessel. As the flanges 22 and 23 are, in turn, deformed upwardly during entry, they tightly engage the inside wall of the vessel to provide a seal between the outer edge of the head and the vessel.

As the head 20 is forced into vessel 29, and into the blood sample to a position wherein the flange 22 is at the interface between the serum and cell fractions, the serum fraction is forced through the filter 27, orifice tube 13 and passage 17 into the collection tube 10. The spray guard 16 diverts flow from tube 13 into passage 17 and keeps the serum from being forced out of the top of the collection tube.

When the flange 22 is positioned at the interface between the sample fractions, the head 20 serves as an essentially permanent barrier between the fractions. Thus, unless the head 20 is pushed further into the receptacle to thereby also force some of the cell fraction through filter 27 and into collection tube 10, the serum fraction can be poured from the collection tube, without contamination from the cell fraction. During such a pour, with the collection tube fully inserted into the head, differential pressure on the cell side of the head and the serum side or interior of the collection tube will keep the cell fraction from moving through the orifice tube.

If it is desired that some or all of the serum fraction be kept in the vessel 29 the collection tube 10 can be withdrawn from vessel 29 while head 20 remains therein as a barrier between sample fractions. The frictional engagement of the flanges 22 and 23 with the wall of vessel 29 holds the head against withdrawal as the collection tube is pulled from the ring portion 28 and orifice tube 13 is pulled from bore 24. As the orifice tube is withdrawn, the portion of the head 20 surrounding bore 24 is expanded into the bore to effectively seal it off, thereby making the head 20 impervious to fluids in the vessel 29. The small diameter and small diameter to length ratio of the bore 24 also tends to prevent unwanted flow through the bore. As the collection tube 10 is withdrawn the serum that has moved through the orifice tube and into the collection tube moves back through the drain holes 19 to collect above the head 20. During withdrawal of the tube 10 a pressure differential is formed across the flexible ring 14 and the bottom of tube 10 to positively move serum from tube 10 into vessel 29.

The collection tube 10 can be fully removed from the sample vessel, which can then be stoppered and transported or stored, with the sample fractions permanently separated and with the serum fraction available to be poured off whenever needed.

Alternatively, the collection tube can be partially removed from the serum fraction, with the volume remaining in the collection tube being indicated by the markings 18 and with that volume being poured off, merely by tipping of the collection tube and partially inserted sample vessel. The portion of the serum fraction between the head 20 and the partially withdrawn collection tube is held within the collection tube by the differential pressures occurring on the opposite sides of end 12 of the collection tube.

The ring 14 engages the wall of the sample vessel and prevents flow around the collection tube and allows the collection tube to act as a piston in forcing serum through the openings 19 and orifice 13 as the collection tube is moved back into the sample vessel after the head 20 has been positioned and the collection tube has been once withdrawn.

With the present invention serum from a spun blood sample in a sample vessel is initially filtered and moved into the collection tube. An essentially permanent barrier is positioned between the cell fraction and the serum fraction of the blood sample and all or any portion of the serum fraction can be removed, as and when desired from the sample vessel.

A sample cup 32 can also be telescoped over the otherwise open end of tube 10 to receive measured amounts of serum when the tube 10 is inverted to pour serum therefrom. The rim of cup 32 rests on a collar 33 of tube 10 and the cup fits snugly over the end of the tube. Transfer of the serum from tube 10 to a sample tube of the type conventionally used in making analysis can thus be accomplished with virtually no chance of contamination to the user.

Although a preferred form of our invention has been herein disclosed, it is to be understood that the present disclosure is made by way of example, and that variations are possible without departing from the subject matter coming within the scope of the following claims, which subject matter we regard as our invention.

We claim:

1. Apparatus for permanently separating the serum fraction from the cell fraction of a spun blood sample in a sample vessel comprising
   a collection tube having a small diameter orifice tube projecting from one end thereof; and
   a head releasably fitted on the one end of the collection tube and having at least one sealing flange extending outwardly therefrom to sealingly engage the wall of the sample vessel and to immobilize the head as the collection tube is withdrawn therefrom, a bore hole extending through said head and having diameter smaller than the outer diameter of the orifice tube but expanding when said orifice tube is inserted thereinto to effectively seal when said orifice tube is removed therefrom and said sealing flange is compressed within the sample vessel.

2. Apparatus as in claim 1, further including means to filter liquid passed through the orifice tube.

3. Apparatus as in claim 1, wherein
   the head has a central chamber at one end of the bore hole and a counterbore opening into the central chamber from one side of the head; and wherein
   the means to filter liquid passed through the orifice tube comprises a filter in the counterbore.

4. Apparatus as in claim 1, further including
   drain ports through the end of the collection tube from which the orifice tube projects and a flexible sealing flange projecting outwardly of the collection tube adjacent to the drain ports to sealingly engage the wall of the sample vessel.

5. Apparatus as in claim 1, further including
   a spray guard within the collection tube and extending over the orifice tube to direct liquid entering the collection tube into the lower end thereof.

6. Apparatus as in claim 5, further including
   means to filter liquid passed through the orifice tube.

7. Apparatus as in claim 6, wherein
   the head has a central chamber at one end of the bore hole and a counterbore opening into the central chamber from one side of the head; and wherein
   the means to filter liquid passed through the orifice tube comprises a filter in the counterbore.

8. Apparatus as in claim 7, further including
   drain ports through the end of the collection tube from which the orifice tube projects and a flexible sealing flange projecting outwardly of the collection tube adjacent to the drain ports to sealingly engage the wall of the sample vessel.

9. Apparatus for handling blood samples comprising
   a sample vessel comprising a tube having one closed end and one open end;
   a collection tube having an outside diameter smaller than the inside diameter of the sample vessel, one open end and a small diameter orifice tube projecting from the opposite end thereof; and
   a flexible head releasably fitted on the one end of the collection tube and having at least one sealing flange extending outwardly therefrom to sealingly engage the wall of said sample vessel and to immobilize the head as the collection tube is withdrawn therefrom, a bore hole extending through said head, said bore hole having a diameter smaller than the outer diameter of the orifice tube but expanding when said orifice tube is inserted thereinto and effectively sealing when said orifice tube is removed therefrom.

10. Apparatus as in claim 9, further including
    means to filter liquid passed through the orifice tube.

11. Apparatus as in claim 10, wherein
    the head has a central chamber at one end of the bore hole and a counterbore opening into the central chamber from one side of the head; and wherein
    the means to filter liquid passed through the orifice tube comprises a filter in the counterbore.

12. Apparatus as in claim 9, further including
    drain ports through the end of the collection tube from which the orifice tube projects and a flexible sealing flange projecting outwardly of the collection tube adjacent to the drain ports to sealingly engage the wall of the sample vessel.

13. Apparatus as in claim 9, further including
    a spray guard within the collection tube and extending over the orifice tube to direct liquid entering the collection tube into the lower end thereof.

14. Apparatus as in claim 13, further including
    means to filter liquid passed through the orifice tube.

15. Apparatus as in claim 14, wherein
    the head has a central chamber at one end of the bore hole and a counterbore opening into the central chamber from one side of the head; and wherein
    the means to filter liquid passed through the orifice tube comprises a filter in the counterbore.

16. Apparatus as in claim 15, further including
    drain ports through the end of the collection tube from which the orifice tube projects and a flexible sealing flange projecting outwardly of the collection tube adjacent to the drain ports to sealingly engage the wall of the sample vessel.

17. Apparatus as in claim 16, further including
    a collar near the outer end of the collection tube remote from the head; and
    a sample cup arranged to be telescopingly inverted over the open end of said collection tube to closely engage the collection tube and to abut against the collar, whereby fluids collected in the collection tube can be transferred to the sample cup by inverting the collection tube.

18. A method of separating the serum fraction from the cell fraction of a spun blood sample in a sample vessel, comprising
    moving a barrier within the sample vessel to a position between the serum and cell fractions while moving the serum fraction through a filter and the barrier into a collection tube;
    removing the collection tube and blocking flow through the barrier, while leaving the barrier positioned in the sample vessel;
    sealing flow between the outer surface of the collection tube and the inner surface of the sample vessel during movement of the collection tube into and out of the sample vessel; and
    draining serum from the collection tube onto the barrier during removal of the collection tube from the sample vessel.

* * * * *